(12) United States Patent
Yu

(10) Patent No.: US 10,085,831 B2
(45) Date of Patent: Oct. 2, 2018

(54) ARTIFICIAL BREAST IMPLANT PROVIDED ON THE SURFACE THEREOF WITH SILICONE OPEN CELL FOAM LAYER, AND METHOD FOR PRODUCING THE SAME

(71) Applicant: Won Seok Yu, Daejeon (KR)

(72) Inventor: Won Seok Yu, Daejeon (KR)

( * ) Notice: Subject to any disclaimer, the term of this patent is extended or adjusted under 35 U.S.C. 154(b) by 508 days.

(21) Appl. No.: 13/923,984

(22) Filed: Jun. 21, 2013

(65) Prior Publication Data

US 2013/0302510 A1    Nov. 14, 2013

Related U.S. Application Data

(63) Continuation of application No. 13/488,552, filed on Jun. 5, 2012, now abandoned, and a continuation of application No. PCT/KR2010/001826, filed on Apr. 12, 2010.

(30) Foreign Application Priority Data

Nov. 19, 2009  (KR) .................. 10-2009-0112022

(51) Int. Cl.
| | |
|---|---|
| *A61F 2/12* | (2006.01) |
| *A61F 2/00* | (2006.01) |
| *B29C 41/14* | (2006.01) |
| *B29C 44/00* | (2006.01) |
| *B29C 67/20* | (2006.01) |
| *B29K 83/00* | (2006.01) |
| *B29L 31/00* | (2006.01) |

(52) U.S. Cl.
CPC .............. *A61F 2/12* (2013.01); *A61F 2/0077* (2013.01); *B29C 41/14* (2013.01); *B29C 44/005* (2013.01); *B29C 67/202* (2013.01); *B29K 2083/005* (2013.01); *B29L 2031/7532* (2013.01)

(58) Field of Classification Search
CPC ........... B29C 41/14; A61F 2/0077; A61F 2/12
USPC ......................................... 156/242; 427/2.24
See application file for complete search history.

(56) References Cited

U.S. PATENT DOCUMENTS

| 3,366,975 | A | * | 2/1968 | Pangman ................... A61F 2/12 128/DIG. 21 |
| --- | --- | --- | --- | --- |
| 5,545,220 | A | * | 8/1996 | Andrews .................... A61F 2/12 427/2.24 |
| 5,571,183 | A | * | 11/1996 | Kazem ...................... A61F 2/12 623/23.67 |
| 5,589,176 | A | * | 12/1996 | Seare, Jr. ................ A61L 27/08 424/400 |
| 2009/0118829 | A1 | * | 5/2009 | Powell ...................... A61F 2/12 427/2.24 |
| 2010/0292790 | A1 | * | 11/2010 | Stroumpoulis ....... A61F 2/0077 427/2.24 |

(Continued)

*Primary Examiner* — Philip C Tucker
*Assistant Examiner* — John Blades
(74) *Attorney, Agent, or Firm* — Park & Associates IP Law, P.C.

(57) ABSTRACT

Disclosed are an artificial breast implant in which the surface thereof is formed or modified with a silicone open cell (open pore) foam layer, and a method for producing the same. More specifically, disclosed are an artificial breast implant that has a surface including an open cell foam layer made of silicone and thus minimizes side effects such as in vivo rejection, which may occur after implantation of the implant into the body, in particular, the occurrence of capsular contracture to achieve superior biocompatibility and safety, and a method for producing the same.

6 Claims, 6 Drawing Sheets

(56) References Cited

U.S. PATENT DOCUMENTS

2013/0302511 A1* 11/2013 Goraltchouk .......... A61L 27/30
427/2.24
2015/0132469 A1* 5/2015 Goraltchouk .......... B05D 3/107
427/2.24

* cited by examiner

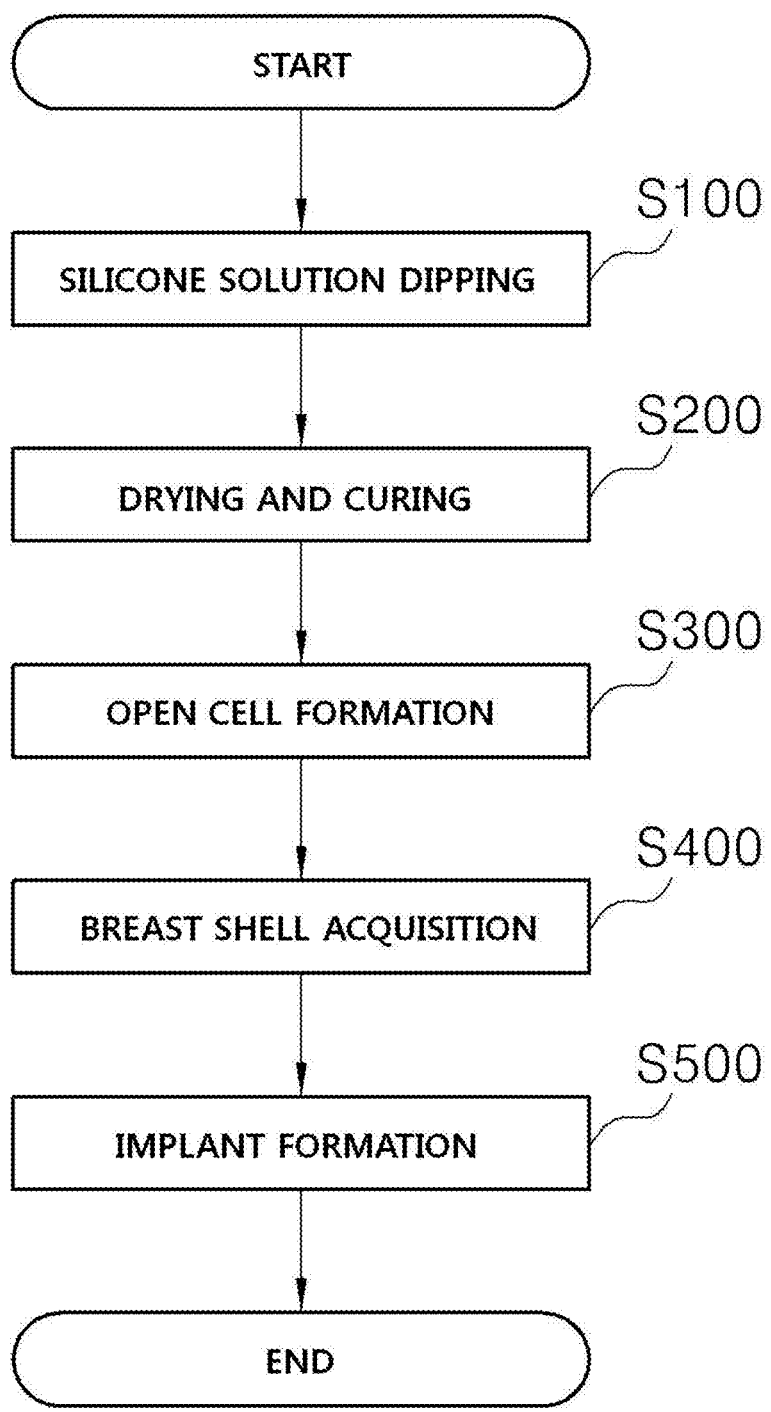

ARTIFICIAL BREAST IMPLANT PROVIDED ON THE SURFACE THEREOF WITH SILICONE OPEN CELL FOAM LAYER, AND METHOD FOR PRODUCING THE SAME

REFERENCE TO RELATED APPLICATIONS

This is a continuation of U.S. patent application Ser. No. 13/488,552 filed on Jun. 5, 2012, which is a continuation of International Patent Application PCT/KR2010/001826 filed on Apr. 12, 2010 and designating the United States and claims priority of Korean Patent Application No. 10-2009-0112022 filed on Nov. 19, 2009, the entire contents of which are incorporated herein by reference.

FIELD OF THE INVENTION

The present invention relates to an artificial breast implant, the surface of which is formed or modified with a silicone open cell (open pore) foam layer, and a method for producing the same. More specifically, the present invention relates to an artificial breast implant that has an open cell foam layer made of silicone on the surface thereof and thus minimizes side effects such as in vivo rejection, which may occur after insertion of the implant into the human body, in particular, the occurrence of capsular contracture to achieve superior biocompatibility and safety, and a method for producing the same.

BACKGROUND OF THE INVENTION

In general, artificial breast prostheses are used in reconstructive plastic surgery for a breast when breast loss occurs due to diseases or accidents and in cosmetic surgery for a malformed breast. In terms of anatomy, artificial breast prostheses are also used for the substitution of organs or tissues.

Artificial breast prostheses are products in which a filling material, such as saline, hydro-gel, and silicone gel, is filled in an envelope formed of silicone that is implantable to an organ (hereinafter referred to as a "shell"). These artificial breast prostheses may be classified into round products and water drop shaped products according to the shape of a product, and may be classified into smooth products and textured products according to the surface conditions of a product. More particularly, the artificial breast prostheses will be described in brief as follows.

A saline filled artificial breast prosthesis is configured such that saline is injected or is injectable into a shell formed of silicone (more particularly, the shell being formed of polyorganosiloxane, such as polydimethylsiloxane or polydiphenylsiloxane). The saline filled artificial breast prosthesis has a structure consisting of a silicone shell and a valve.

Although the saline filled artificial breast prosthesis ensures safety of a user even if the filling material leaks into the human body after rupture of the shell as a result of using sterile saline as the filling material, and is easy to change the volume of a breast by adjusting the injection amount of saline, the saline filled artificial breast prosthesis is significantly deteriorated to the touch after surgery as compared to other artificial breast prostheses and the shell thereof has inferior durability.

A hydro-gel filled artificial breast prosthesis is configured such that hydro-gel composed of monosaccharide and polysaccharides is filled within the same shell as that used in the above described saline filled artificial breast prosthesis. The hydro-gel filled artificial breast prosthesis is a product developed based on the principle that the filling material can be absorbed into and excreted from the human body even if the filling material leaks into the human body due to rupture of the shell.

However, in the case of the hydro-gel filled artificial breast prosthesis, safety with respect to long term use has not been established, volume change depending on the lapse of time and occurrence of wrinkles may increase after the artificial breast prosthesis is inserted into the human body, and feeling is unnatural as compared to a silicone gel filled artificial breast prosthesis. At present, the above described hydro-gel filled artificial breast prostheses are not distributed on the market on the basis of the year 2000 due to problems in relation to the proof of safety.

A silicone gel filled artificial breast prosthesis is configured such that silicone gel having an appropriate viscosity is filled in a shell. The silicone gel filled artificial breast prosthesis has very superior product durability and more pleasant texture than the saline filled artificial breast prosthesis, and owing to these advantages, has achieved a dominant position in the market.

The silicone gel filled artificial breast prosthesis has been developed in the order of a first generation prosthesis, a second generation prosthesis, and a third generation prosthesis. This development history will be described in detail as follows.

The first generation silicone gel filled artificial breast prosthesis is a product sold from the middle of the 1960s to the middle of the 1970s, and was initially developed in the year 1961 by Cronin and Gerow. The first generation silicone gel filled artificial breast prosthesis can be represented in brief by use of a thick shell, a smooth surface type, and silicone gel of a high viscosity. This prosthesis has caused gel bleed and capsular contracture, but a rupture speed thereof was relatively low due to the use of the thick shell.

The second generation silicone gel filled artificial breast prosthesis is a product sold from the middle of the 1970s to the middle of the 1980s, and includes a thin shell and a silicone gel filling material of a low viscosity, for the sake of smoother texture. This prosthesis is characterized by a similar gel bleed rate, higher rupture occurrence, and lower capsular contracture as compared to the first generation prosthesis.

The third generation silicone gel filled artificial breast prosthesis is a product sold from the middle of the 1980s to present, and includes a gel bleed barrier layer to prevent gel bleed. The third generation silicone gel filled artificial breast prosthesis includes a thicker shell and silicone gel of a higher viscosity as compared to the second generation prosthesis. In addition, a product having a rough surface has been developed, in order to reduce capsular contracture. The third generation silicone gel filled artificial breast prosthesis exhibit low rupture and low capsular contracture occurrence, as compared to the first and second silicone gel filled artificial breast prostheses.

As defined above, development and progress in terms of artificial breast prosthesis safety have focused on decrease in rupture and capsular contracture. This is a natural result, when taking into consideration the fact that rupture and capsular contracture are the greatest side effects of artificial breast prostheses.

These two side effects, that is, rupture and capsular contracture will be described. First, in the case of rupture, an event in which Dow Corning sold the prosthesis was bankrupted due to rupture of a great amount of the second generation silicone gel filled artificial breast prosthesis using a thin shell is well-known. The filling material (silicone gel)

of the artificial breast prosthesis may leak into the body through the ruptured shell, deformation and malfunction of the prosthesis thus occur, and, as a result, the prosthesis is removed.

Second, capsular contracture is a natural biological rejection reaction in which collagen films are firmly accumulated around a prosthesis, after insertion of the implant into the human body, which is observed in all patients that undergo artificial breast prosthesis surgery, but there is a difference in severity of capsular contracture therebetween. Prostheses are removed from patients that suffer from serious capsular contracture.

Considering prosthesis removal operation caused by side effects according to various causes, capsular contracture is known to be the most significant side effect of artificial breast prostheses, which is demonstrated from various clinical papers published for a long time.

In accordance with continuous research and progress of artificial breast prostheses, for capsular contracture which is a side effect having high onset and high re-operation, prostheses capable of reducing the onset and reoperation is developed. As a result, the third generation artificial breast prostheses have emerged, and textured surface artificial breast implants in which the surface thereof is roughly formed or modified in order to reduce capsular contracture were developed and distributed in the market.

Such a textured artificial breast implant minimizes hardening of collagen films deposited on the surface thereof, thus minimizing occurrence of capsular contracture. Various methods to form a rough surface of an artificial breast implant have been developed to date. However, methods having commercial availability are classified into four forms, that is, urethane foam, solid particle, processed mold, and pressed mold forms.

Of these, artificial breast implants in which urethane foams developed by methods described in U.S. Pat. No. 3,366,975 and U.S. Pat. No. 3,683,424 formed on the surfaces thereof are known to exhibit the greatest effects on reduction of capsular contracture, but such a method and product are not used at present due to the problem associated with safety of urethane in the body.

U.S. Pat. No. 4,889,744, U.S. Pat. No. 5,545,220, and U.S. Pat. No. 5,964,803 disclose methods for forming artificial breast implants having a textured (rough) surface, by adhering solid particles to artificial breast shells, or adhering solid particles to artificial breast shells, followed by melting.

U.S. Pat. No. 4,965,430 discloses a method for producing artificial breast implants with a textured surface, by forming a textured surface on a mold used for preparation of an artificial breast implant.

U.S. Pat. No. 4,960,425, U.S. Pat. No. 4,955,909, U.S. Pat. No. 5,022,942, and U.S. Pat. No. 5,236,453 disclose methods for producing an artificial breast implant having a textured surface by adhering a film surface-roughened through a mold or ion beam to an artificial breast shell using a press mold.

Of these methods, except the method of forming a urethane foam on the surface of an artificial breast, other methods simply make the surface of the artificial breast rough and have lower efficacy in terms of reduction of capsular contracture as compared to urethane foam artificial breasts.

The reason for this is that except the method of forming a urethane foam on the surface of to artificial breast, other methods are low in uniform deposition and hardening prevention of collagen films on the surface of implants, as compared to urethane implants, since a textured surface form, more specifically, textured mono-layer, not a foam layer, is formed on the surface of the artificial breast.

As described above, the development and progress in terms of safety of silicone artificial breast implants have focused on decrease in rupture and capsular contracture, but methods developed to date are not complete in technical regards, and in particular, have a high capsular contracture onset as a side effect, thus entailing considerably frequent removal and re-operation of the implants. This fact is clinically demonstrated.

Accordingly, development of artificial breast implants that are capable of reducing capsular contracture and exhibit superior durability remains as a problem that should be urgently and completely solved.

SUMMARY OF THE INVENTION

The present invention has been made in view of the above problems of the related art, and it is one object of the present invention to provide an artificial breast implant that minimizes capsular contracture, which may occur after insertion of the implant into the human body, and thus achieves superior biocompatibility and safety.

It is another object of the present invention to provide an artificial breast implant that minimizes occurrence of capsular contracture and exhibits superior durability.

To solve the above described technical objects and in accordance with one embodiment of the present invention, an artificial breast implant of the present invention is characterized in that a silicone open cell (open pore) foam layer is formed or modified on the surface of an implant shell with a uniform thickness.

According to the present invention, the artificial breast implant includes a silicone open cell foam layer on the surface thereof, thus minimizing a side effect such as capsular contracture, which may occur after insertion of the implant into the human body. In addition, the artificial breast implant includes a silicone foam layer with a uniform thickness present on the silicone shell, thus preventing occurrence of stress concentration, and exhibiting superior durability, as compared to conventional textured surface silicone artificial breast implants.

BRIEF DESCRIPTION OF THE DRAWINGS

FIG. 11 is a block diagram illustrating a method for producing a silicone artificial breast implant provided with a silicone open cell foam according to one embodiment of the present invention.

DESCRIPTION OF REFERENCE NUMERALS OF IMPORTANT PARTS OF THE DRAWINGS

10: silicone Shell 20, 30, 40: protrusion 50: pore, cell 60: silicone open cell foam 70: silicone open cell foam layer.

DETAILED DESCRIPTION OF THE INVENTION

The artificial breast implant of the present invention is characterized in that the artificial breast implant is provided on the surface thereof with a silicone open cell foam layer, wherein the silicone open cell foam layer with a uniform thickness is disposed on a silicone shell with a uniform thickness.

Hereinafter, the present invention will be described in detail with reference to the annexed drawings.

Figure 1:
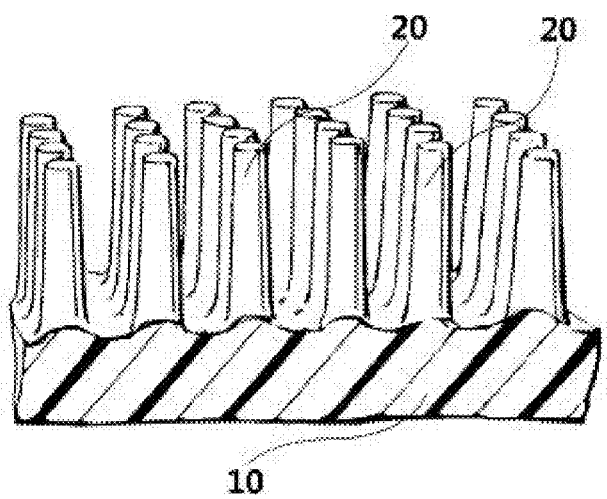
FIG. 1 is a cross-sectional view illustrating the structure of a conventional textured surface silicone artificial breast implant.
Figure 2:
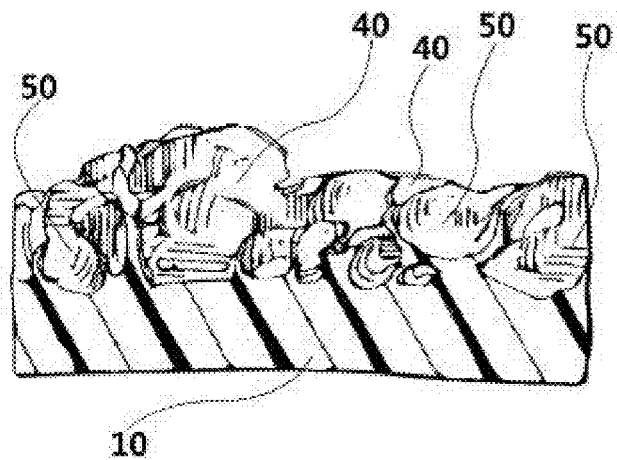
FIG. 2 is a cross-sectional view illustrating the structure of a conventional textured surface silicone artificial breast implant.
Figure 3:
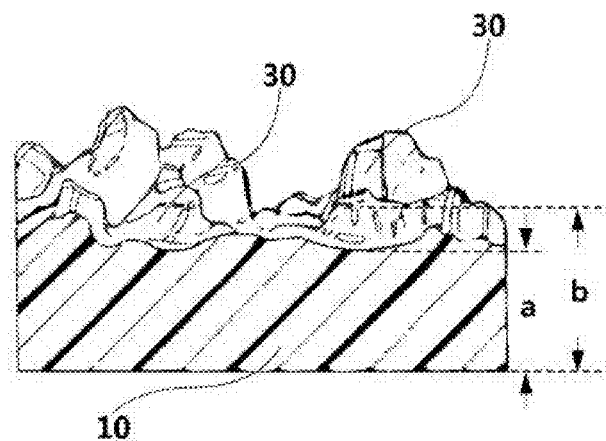
FIG. 3 is a cross-sectional view illustrating the structure of a conventional textured surface silicone artificial breast implant.

FIGS. 1, 2 and 3 are cross-sectional views illustrating the structure of a conventional textured surface silicone artificial breast implant.

Specifically, FIG. 1 shows a textured surface silicone artificial breast implant which is produced by etching a sheet 10 provided with a protrusion 20 to the surface of an artificial breast implant using a press mold or by etching the surface of the implant using an ion-beam thruster, and the surface thereof has a very simple structure, as compared to the surface of the textured surface silicone artificial breast implant surface, produced by another method. Accordingly, a textured surface implant to reduce capsular contracture has lower efficacy than other textured surface implants.

FIG. 2 shows a textured surface implant that is produced by etching the surface thereof using a solid particle, has a complicated surface structure, and a dense protrusion structure, as compared to the surface of implant of FIG. 1. However, this implant also has a limitation in that the protrusion 40 of the surface is in the form of a monolayer surface, not a foam, as shown in the drawing, has a non-uniform shell thickness and thus entails occurrence of stress concentration due to presence of protrusions 40 and 50, thus causing a deterioration in durability of shells, that is, implants.

FIG. 3 shows a textured surface implant that is produced by adhering a solid particle or using an etched mold. This implant also has a relatively simple surface structure, has a shell 10 with a considerably non-uniform thickness, as shown from thickness difference between surfaces a and b, and has an implant durability problem due to stress concentration.

Figure 4:
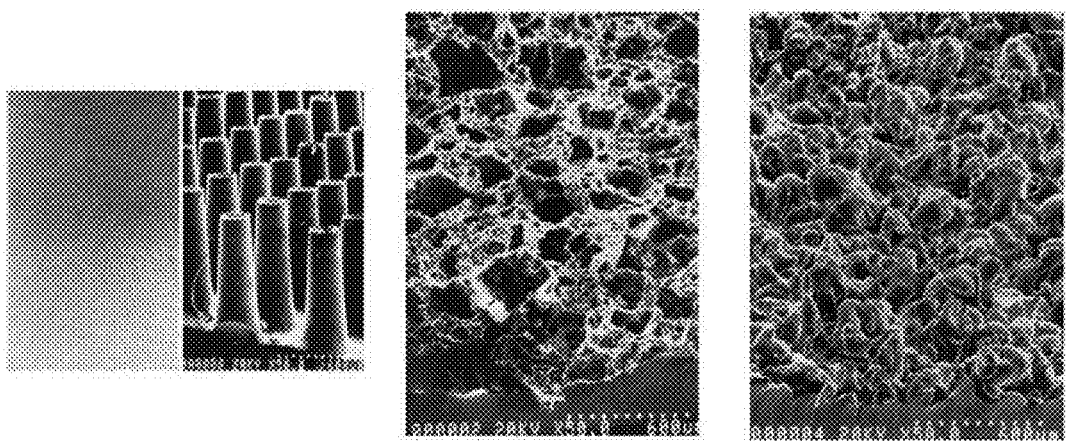
FIG. 4 is a surface microscope image illustrating a conventional textured surface silicone artificial breast implant.
Figure 5:
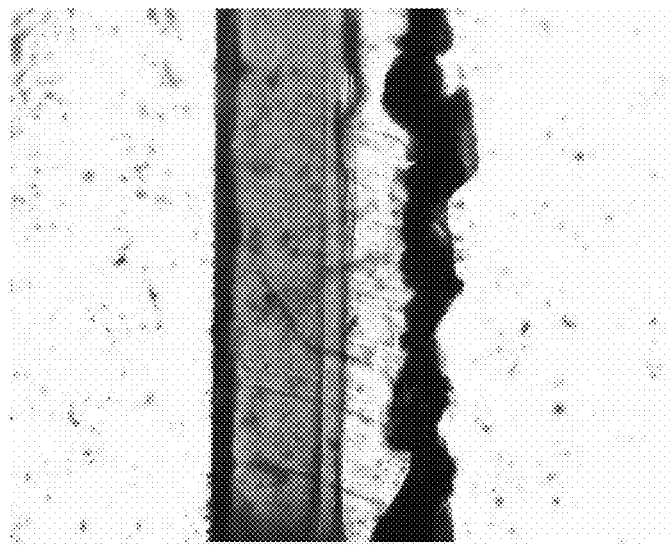
FIG. 5 is a cross-sectional surface microscope image illustrating a conventional textured surface silicone artificial breast implant.

FIG. 4 is a surface microscope image illustrating a conventional textured surface silicone artificial breast implant. From FIG. 4, it can be seen that the implant is provided on the surface thereof with monolayer-shaped regular or irregular protrusions. FIG. 5 is a cross-section surface microscope image of a conventional textured surface silicone artificial breast implant. From FIG. 5, it can be seen that the shell has a non-uniform thickness and has cracks, which may be a break point, present in the center of the shell.

Figure 6:
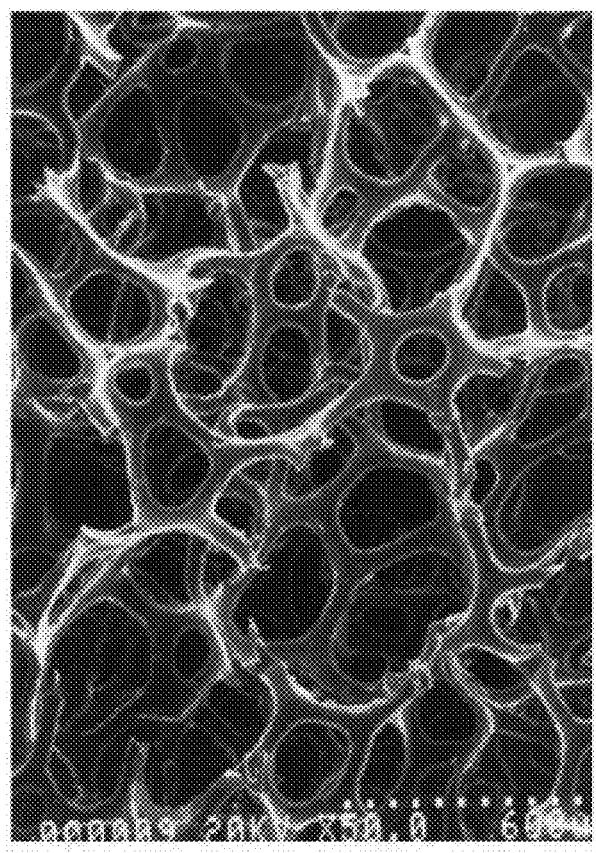
FIG. 6 is a surface electron microscope image illustrating a conventional urethane-coated silicone artificial breast implant.

FIG. 6 is a surface electron microscope image illustrating a conventional urethane-coated foam-type silicone artificial breast implant. From FIG. 6, it can be seen that a cell has a complicated three-dimensional net structure.

As described above, such conventional textured surface artificial breast implants are ineffective for reducing capsular contracture, have low durability, or have a safety problem, such as urethane-coated implants.

Figure 7:
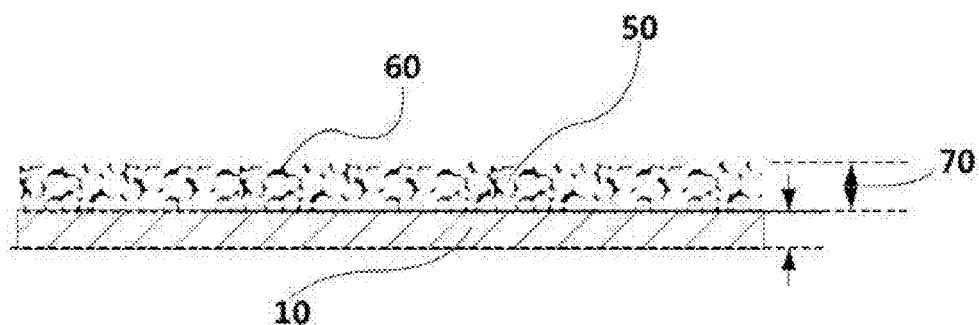
FIG. 7 is a cross-sectional view illustrating a silicone artificial breast implant provided with a silicone open cell foam according to the present invention.

However, as shown in FIG. 7, the artificial breast implant of the present invention has a characteristic configuration in which a silicone open cell foam layer 70 with a uniform thickness is disposed on a silicone shell 10 with a uniform thickness, and all components of the artificial breast implant of the present invention are made of polyorganosiloxane.

The polyorganosiloxane used for the artificial breast implant uses the following materials as materials having an implant grade capable of securing safety after implantation into the human body.

Basically, polyorganosiloxane has a structure in which a main chain is silane, and an organic group such as a methyl group is bonded to the silane main chain.

The most representative example is polydimethylsiloxane in which a methyl group is bonded to the main chain. The methyl group of dimethylsiloxane which is a monomer of polydimethylsiloxane may be substituted by an organic group such as alkyl group, phenyl group, or vinyl group.

For example, the dimethylsiloxane is substituted by methyl hydrogen siloxane, methyl phenyl siloxane, diphenyl siloxane, dimethyl vinyl siloxane, tri-fluoropropyl siloxane or the like, and polymers can be prepared by polymerization of these monomers and used. Also, copolymers using oligomers comprising these monomers can be produced and used.

Figure 8:
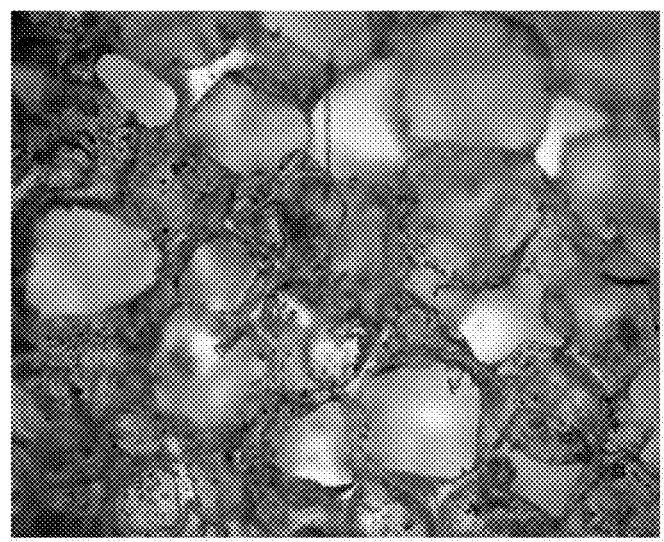
FIG. 8 is a surface microscope image illustrating a silicone artificial breast implant provided with a silicone open cell foam according to the present invention.
Figure 9:
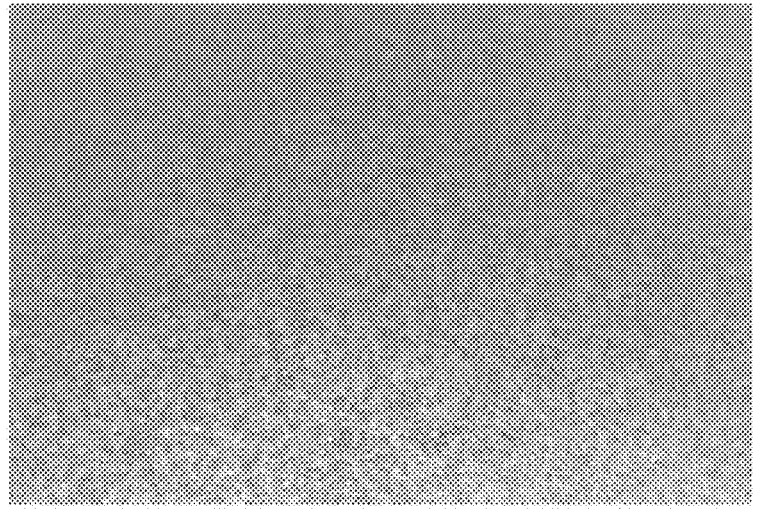
FIG. 9 is a surface image illustrating a silicone artificial breast implant provided with a silicone open cell foam according to the present invention.
Figure 10:
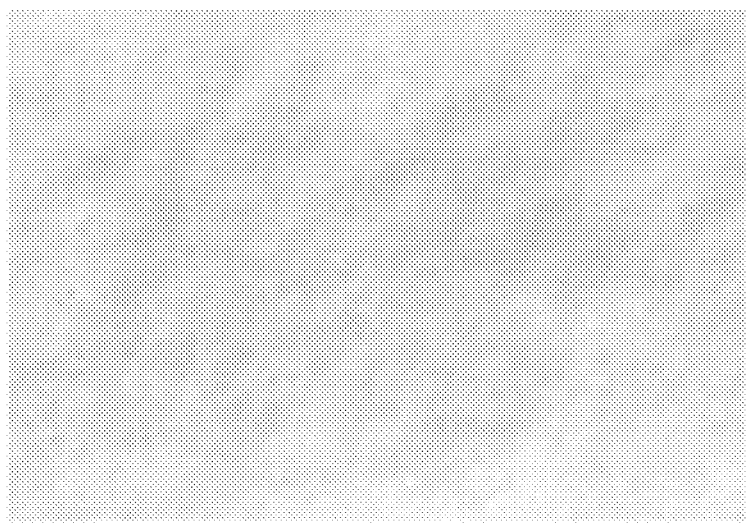
FIG. 10 is a surface image illustrating a silicone artificial breast implant provided with a silicone open cell foam according to the present invention.

FIG. 8 is a surface microscope image illustrating a silicone artificial breast implant provided with a silicone open cell foam. An open cell 50 of FIG. 7 has a three-dimensional net structure. FIG. 9 is a surface image illustrating a silicone artificial breast implant provided with a silicone open cell foam, which shows a state in which a foam layer with a considerably thin thickness (mean height: 300 um) is formed. FIG. 10 is a surface image illustrating a silicone artificial breast implant provided with a silicone open cell foam, which shows a state in which a foam layer with a suitable thickness (mean height: 1,500 um) is formed.

The silicone open cell foam layer formed on the surface of the implant according to the present invention prevents hardening of collagen films deposited around the implant after insertion into the human body and thus prevents occurrence of capsular contracture. In addition, although collagen films are deposited around the implant, collagen is grown in the open cell foam layer formed on the implant and a sponge-like structure is formed, not a hard plate-shaped structure.

Accordingly, collagen tissues having an elasticity similar to other human body tissues are formed and occurrence of capsular contracture can thus be minimized. Furthermore, after insertion of an implant into the human body, the implant is rapidly fixed on the operation site due to ingrowth of collagen in the implant and recovery of patients can be also facilitated.

Meanwhile, the artificial breast implant provided with a silicone open cell foam layer according to the present invention is produced by a method including:

a silicone dipping operation of dipping a breast-shaped mold in a silicone solution to obtain an artificial breast shell (S100);

a drying and curing operation of drying an artificial breast shell adhered to the mold using a drier, followed by curing, to obtain a silicone artificial breast shell (S200);

an open cell formation operation of forming an open cell foam layer on the surface of the dried and cured shell (S300);

an artificial breast shell acquisition operation of forming an aperture on the bottom of the artificial breast shell adhered to the mold and provided with the open cell foam layer and removing the artificial breast shell from the mold (S400); and an implant formation operation of adhering a silicone film including a leakage prevention film to the aperture to fill the aperture (S500).

Hereinafter, a method for producing an artificial breast implant provided with the silicone open cell foam layer according to the present invention will be described in more detail.

First, a breast-shaped mold is treated with a silicone solution by dipping or the like, to obtain an artificial breast shell (S100)

The mold is taken out in the silicone solution, dried and cured to obtain a silicone artificial breast shell. For example, the artificial breast shell is dried and cured in a drier such as an oven (S200).

An open cell foam layer is formed on the dried and cured artificial breast shell (S300).

More specifically, the formation of the open cell foam layer is carried out by dipping the dried and cured mold provided with the shell in a silicone solution to form a silicone solution film on the surface of the shell, and treating the surface of the shell by scattering or spraying, to the surface of the shell, a solid particle or powder with an appropriate size such that the silicone solution film loses its flowability.

At this time, the solid particle or powder is not affected by the silicone solution and is not dissolved. In addition, the solid particle or powder that does not affect physical properties of silicone which contacts the solid particle or powder is used. Consequently, with the addition of an appropriate solvent, the solid particles or powder is dissolved and thus removed in the following process. The most preferred solvent is water.

When water is used as the solvent, the solid particle or powder may be selected from but not limited to sodium chloride, ammonium carbonate, ammonium phosphate, ammonium chloride or the like. The most preferred is sodium chloride.

The shell whose surface is entirely stained with the silicone solution and solid particles or powder, that is, the shell-provided mold is treated with an organic solvent by spraying or dipping. At this time, applicable organic solvents are readily miscible with a silicone solution and are generally an aromatic organic solvent or a derivative thereof such as benzene, toluene or xylene, most preferably xylene.

The organic solvent-treated shell is treated with solid particles or powder. The solid powder or particle used herein is completely dried. Through this process, the treated solid particles or powder is soaked by the silicone solution by capillary action.

At this time, an open cell foam layer with desired thickness can be formed by controlling and repeating the concentration of the silicone solution, size of solid particle or powder, and/or organic solvent treatment speed. In addition, the thickness of the open cell foam layer can be controlled by post-processing using a nap-removing apparatus.

Next, after formation of the open cell foam layer, the open cell foam layer is dried and cured. After completion of curing, the open cell foam layer is treated with a solvent such as water to remove the solid particle or powder. At this time, the open cell foam layer may be rubbed by an apparatus causing no nipping such as soft cloth or a brush.

In the process of rubbing, a small amount of close cell which is inevitably produced during formation of foams can be partially removed. The reason for this is that the cell wall of foams is considerably thin. In the process of rubbing, remaining solid particles or powders that are not dissolved in a small amount of close cells are rubbed together via considerably thin cell walls, producing tiny holes on the cell walls to open the close cells.

At this time, the solid particles or powders that are not removed by the rubbing process can be completely removed by repeating permeation of high-pressure water vapor and washing. This process is carried out by extraction-removing remaining solid particles or powders that are not removed, through permeation of water vapor and uses a property in that silicone permeates water vapor. That is, solid particles or powders dissolved in water vapor are changed into those having a small enough size that they can pass through silicone molecules and are then extracted outside, and can be completely removed by repeated extraction and washing operations.

Such water vapor treatment includes direct water vapor treatment in which artificial breast shells are directly treated with water vapor and indirect water vapor treatment in which artificial breast shells are boiled in a container containing water.

In accordance with the formation method of the open cell foam layer according to the present invention, a foam layer is formed using solid particles or powders and organic solvent by capillary action, while forming a foam layer on the cured shell surface. As shown in FIG. 7, the thickness of the uniform shell can be maintained and stress concentration caused by non-uniform shell thickness can be prevented, and shell and implants with superior durability can be obtained.

An aperture is formed on the bottom of the artificial breast shell provided with the open cell foam layer and adhered to the mold, and the artificial breast shell is detached from the mold through the aperture to obtain an artificial breast shell (S400).

Silicone fragments having a similar size to the aperture 128 are adhered to the aperture to fill the aperture and thereby an implant (S500). At this time, adhering of silicone fragments can be carried out by press molding or using a bonding material or the like. This will be easily understood by those skilled in the art of artificial breast implants and a detailed explanation thereof is thus omitted.

Also, all of the contents that are not described in detail in the production method are easily understood by those skilled in the art of producing artificial breast implants and a detailed explanation thereof is thus omitted.

EXAMPLE 1

First, methyl hydrogen siloxane; dimethylsiloxane containing a small amount of platinum catalyst, containing about 20% of a silica filler and having a molecular weight of 50,000 to 100,000 ten thousands; and dimethyl vinyl siloxane containing dimethylvinyl terminated siloxane having a dimethyl group as a terminal group, containing 20% of a silica filler and having a molecular weight of 50,000 to 100,000 ten thousands were sufficiently mixed at an equivalent ratio of methyl hydrogen siloxane to prepare a silicone material.

Xylene as an organic solvent was added to the silicone material silicone such that the concentration of the silicone was 35 wt %, followed by thoroughly mixing to prepare a silicone dilute solution.

Then, a breast-shaped mold for artificial breast shell was treated and coated with the silicone dilute solution by dipping, the organic solvent was completely evaporated at 50° C. in an oven, the mold was dried, and the dried artificial breast mold provided with a silicone coating film was cured in an oven at 170° C. for three hours.

The artificial breast mold provided with a dried silicone coating film was sufficiently cooled at room temperature and treated by dipping in the wt % silicone dilute solution.

Then, the dilute silicone solution-coated artificial breast mold was treated with dried sodium chloride (NaCl) with an average particle size of 500 um by spraying, and an artificial breast mold treated with the silicone dilute solution and sodium chloride was treated with xylene by dipping.

Then, the xylene-treated artificial breast mold was treated with dried sodium chloride (NaCl) with an average particle size of 500 um by spraying, the artificial breast mold treated with sodium chloride was treated with xylene by dipping, and the organic solvent was completely evaporated at 30° C. in an oven, followed by drying.

Then, the xylene-treated artificial breast mold was treated with dried sodium chloride (NaCl) with an average particle size of 200 um by spraying, the artificial breast mold treated with sodium chloride was treated with xylene by dipping, and the organic solvent was completely evaporated at 30° C. in an oven, followed by drying.

Silicone formed on the dried artificial breast mold was completely cured at 170V in an oven for three hours, and the cured artificial breast shell formed on the artificial breast mold was rubbed with a brush in room temperature clear water to remove sodium chloride.

Then, the silicone foam formed on the artificial breast shell surface was processed to a uniform thickness using a nip-removal apparatus to realize excellent appearance and even surface. At this time, the height of foam layer can be post-treated to a desired thickness by the method.

Then, the artificial breast shell was washed with IPA and water in order to remove foreign materials, an aperture was formed on the bottom of the silicone shell of the artificial breast mold, and the silicone shell was detached from the mold and obtained.

Then, to remove incompletely removed sodium chloride, the artificial breast shell was heated in the presence of 140° C. water and 1.4 atm vapor using a high-pressure vapor sterilizer for about 30 hours and the treated artificial breast shell was alternately washed with clear water and IPA.

The high-pressure vapor treatment and washing operations were repeated five times, to obtain a silicone shell provided on the surface thereof with a sodium chloride-completely removed open cell foam layer. An aperture present on the bottom of the silicone shell provided on the surface thereof with the open cell foam layer was adhered and sealed to form an implant shell. The implant-formed shell was filled with silicone gel as a filler using a filling apparatus and cured to produce a silicone artificial breast implant.

Those skilled in the art will appreciate that the above description can be implemented in other detailed embodiments without changing technical ideas or essential characteristics of the present invention. Therefore, it should be understood that the above described embodiments are given only by way of example and the present invention is not limited thereto.

Accordingly, the scope of the present invention is defined by the accompanying claims other than the above detailed description, and all modifications or alternatives deduced from the spirit and scope of the invention as defined by the claims and equivalent concepts thereof should be construed as being included in the scope of the present invention.

What is claimed is:

1. A method for producing an artificial breast implant comprising the processes of:
   dipping a breast-shaped mold in a silicone solution;
   drying and curing the silicon solution adhered to the mold, and thereby forming a cured silicone shell;
   forming an open cell foam layer on an outer surface of the cured silicone shell;
   forming an aperture on a bottom of the cured silicone shell, and removing the cured silicone shell from the mold through the aperture, thereby obtaining an artificial breast shell; and
   adhering a silicone film including a leakage prevention film to the aperture to seal the aperture,
   wherein said forming the open cell foam layer process includes the steps of:
   (a) dipping the cured silicone shell adhered to the mold in a second silicone solution, and taking the cured silicone shell out to form a silicone solution film on the outer surface of the cured silicone shell;
   (b) scattering or spraying solid particles or powder with an appropriate size to the surface of the silicone solution film such that the silicone solution film loses flowability;
   (c) spraying or applying by dipping an organic solvent on a resultant product of said step (b); and
   (d) re-scattering or re-spraying solid particles or powder on a resultant product of said step (c),
   wherein, in said forming the open cell foam layer process, the solid particles or powder is not dissolved in the silicone solution and does not affect physical properties of the silicone solution, and is dissolved in a washable solvent and removed thereby,
   wherein said forming the open cell foam layer process is repeated until the open cell foam layer has a desired thickness, in which the desired thickness of the open cell foam layer is obtained by controlling (e) a concentration of silicone solution, (f) an average size of solid particles or powders, the average size being changeable at selected repetition steps of said forming, and (g) an organic solvent spraying speed,
   wherein, in said forming the open cell foam layer process, the treated solid particles or powder for formation of the open cell are removed by treating the artificial breast shell using washing with water, treating with water vapor, heating and high-pressure vapor treating the artificial breast shell provided with dried and cured open cell foam layer in the presence of 140° C. water and 1.4 atm vapor pressure, for about 30 hours, to remove incompletely removed solid particles or powder from the artificial breast shell.

2. The method of claim 1, wherein the solid particles or powder is sodium chloride, ammonium carbonate, ammonium phosphate, or ammonium chloride.

3. The method of claim 1, wherein the organic solvent is benzene, toluene, or xylene.

4. The method of claim 1, wherein the washable solvent is water.

5. The method of claim 1, wherein said forming the open cell foam layer process further includes drying and curing the formed open cell foam layer.

6. A method for producing an artificial breast implant comprising the processes of:
dipping a breast-shaped mold in a silicone solution;
drying and curing the silicon solution adhered to the mold, and thereby forming a cured silicone shell;
forming an open cell foam layer on an outer surface of the cured silicone shell;
forming an aperture on a bottom of the cured silicone shell, and removing the cured silicone shell from the mold through the aperture, thereby obtaining an artificial breast shell; and
adhering a silicone film including a leakage prevention film to the aperture to seal the aperture,
wherein said forming the open cell foam layer process includes the steps of:
(a) dipping the cured silicone shell adhered to the mold in a second silicone solution, and taking the cured silicone shell out to form a silicone solution film on the outer surface of the cured silicone shell;
(b) scattering or spraying solid particles or powder with an appropriate size to the surface of the silicone solution film such that the silicone solution film loses flowability;
(c) spraying or applying by dipping an organic solvent on a resultant product of said step (b); and
(d) re-scattering or re-spraying solid particles or powder on a resultant product of said step (c),
wherein, in said forming the open cell foam layer process, the solid particles or powder is not dissolved in the silicone solution and does not affect physical properties of the silicone solution, and is dissolved in a washable solvent and removed thereby,
wherein said forming the open cell foam layer process is repeated until the open cell foam layer has a desired thickness, in which the desired thickness of the open cell foam layer is obtained by controlling (e) a concentration of silicone solution, a size of solid particles or powders, and an organic solvent spraying speed,
wherein, in said forming the open cell foam layer process, the treated solid particles or powder for formation of the open cell are removed by treating the artificial breast shell using washing with water, treating with water vapor, heating and high-pressure vapor treating the artificial breast shell provided with dried and cured open cell foam layer in the presence of 140° C. water and 1.4 atm vapor pressure, for about 30 hours, to remove incompletely removed solid particles or powder from the artificial breast shell.

* * * * *